US010285875B1

(12) United States Patent
Jenkins

(10) Patent No.: US 10,285,875 B1
(45) Date of Patent: May 14, 2019

(54) SKIN-ATTACHED PERSPIRATION ABSORPTION AND CAPTURE SYSTEM

(71) Applicant: Julie W Jenkins, Williamsburg, VA (US)

(72) Inventor: Julie W Jenkins, Williamsburg, VA (US)

( * ) Notice: Subject to any disclaimer, the term of this patent is extended or adjusted under 35 U.S.C. 154(b) by 702 days.

(21) Appl. No.: 14/881,786

(22) Filed: Oct. 13, 2015

Related U.S. Application Data

(60) Provisional application No. 62/064,708, filed on Oct. 16, 2014.

(51) Int. Cl.
*A61F 7/00* (2006.01)
*A61F 13/539* (2006.01)
*A61F 13/15* (2006.01)

(52) U.S. Cl.
CPC ...... *A61F 13/539* (2013.01); *A61F 13/15203* (2013.01); *A61F 2013/15008* (2013.01); *A61F 2013/15487* (2013.01); *A61F 2013/53908* (2013.01)

(58) Field of Classification Search
CPC .............. A41D 13/1176; A61F 13/539; A61F 13/15203; A61F 13/122
See application file for complete search history.

(56) References Cited

U.S. PATENT DOCUMENTS

| | | | | |
|---|---|---|---|---|
| 3,885,247 A | * | 5/1975 | Kost | A41D 27/133 2/55 |
| 6,526,975 B1 | * | 3/2003 | Chung | A41D 13/1176 128/201.17 |
| 2004/0133143 A1 | * | 7/2004 | Burton | A61F 13/0203 602/58 |
| 2010/0191204 A1 | * | 7/2010 | Bach | A61F 5/443 604/344 |
| 2010/0299796 A1 | * | 12/2010 | Hashemian | A41D 27/133 2/53 |
| 2013/0060209 A1 | * | 3/2013 | Tyler | A61F 13/00063 604/307 |

* cited by examiner

*Primary Examiner* — Ariana Zimbouski
(74) *Attorney, Agent, or Firm* — Peter J. Van Bergen

(57) ABSTRACT

A perspiration absorption and capture system includes a fluid permeable adhesive layer, a fluid impermeable layer, and a fluid absorption layer disposed between and coupled to the permeable adhesive layer and the fluid impermeable layer. When the adhesive layer is attached to a user's skin, the absorption layer absorbs perspiration and the impermeable layer locks the perspiration in the absorption layer.

6 Claims, 6 Drawing Sheets

US 10,285,875 B1

SKIN-ATTACHED PERSPIRATION ABSORPTION AND CAPTURE SYSTEM

Pursuant to 35 U.S.C. § 119, the benefit of priority from provisional application 62/064,708, with a filing date of Oct. 16, 2014, is claimed for this non-provisional application.

FIELD OF THE INVENTION

The invention relates generally to perspiration absorbing apparatus, and more particularly to a perspiration absorption and capture system that is attachable to skin surfaces.

BACKGROUND OF THE INVENTION

Perspiration can be generated during one or more of physical exertion, exposure to a high-temperature environment, and exposure to a stressful situation. When perspiration is produced, clothing tends to absorb perspiration from covered areas of the body. However, perspiration produced or collecting at areas of the body that are generally uncovered (e.g., face and hands) is not absorbed and can quickly become an annoyance to a worker, athlete, etc. This is especially true when perspiration drips/runs into one's eyes where the typical reaction is to use one's hands or shirt sleeve to wipe away the perspiration. Wiping perspiration from one's face in this fashion is a distraction and can be dangerous. For example, when someone is working in a hazardous environment (e.g., a nuclear facility) or is working with hazardous substances (e.g., chemicals, paints, etc.), touching one's face or eyes can cause contamination of sensitive body parts (e.g., skin, eyes, mouth, etc.).

SUMMARY OF THE INVENTION

Accordingly, it is an object of the present invention to provide a system for perspiration absorption.

Another object of the present invention is to provide a system that can absorb perspiration on parts of the body that are generally not covered by clothing.

Still another object of the present invention is to provide a perspiration absorption system that is readily positioned on exposed parts of the body.

Other objects and advantages of the present invention will become more obvious hereinafter in the specification and drawings.

In accordance with the present invention, a perspiration absorption and capture system includes a fluid permeable adhesive layer, a fluid impermeable layer, and a fluid absorption layer disposed between and coupled to the permeable adhesive layer and the fluid impermeable layer. The adhesive layer can be attached to a user's skin, the absorption layer then absorbs perspiration from the user's skin, and the impermeable layer locks the perspiration in the absorption layer.

BRIEF DESCRIPTION OF THE DRAWINGS

Other objects, features and advantages of the present invention will become apparent upon reference to the following description of the preferred embodiments and to the drawings, wherein corresponding reference characters indicate corresponding parts throughout the several views of the drawings and wherein.

DETAILED DESCRIPTION OF THE INVENTION

Figure 1:
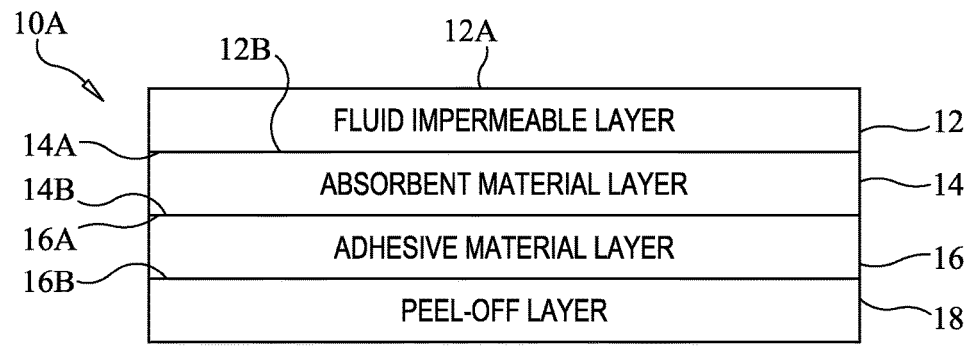
FIG. 1 is a schematic cross-sectional view of a multi-layer perspiration absorption and capture system prior to its use in accordance with an embodiment of the present invention.
Figure 2:
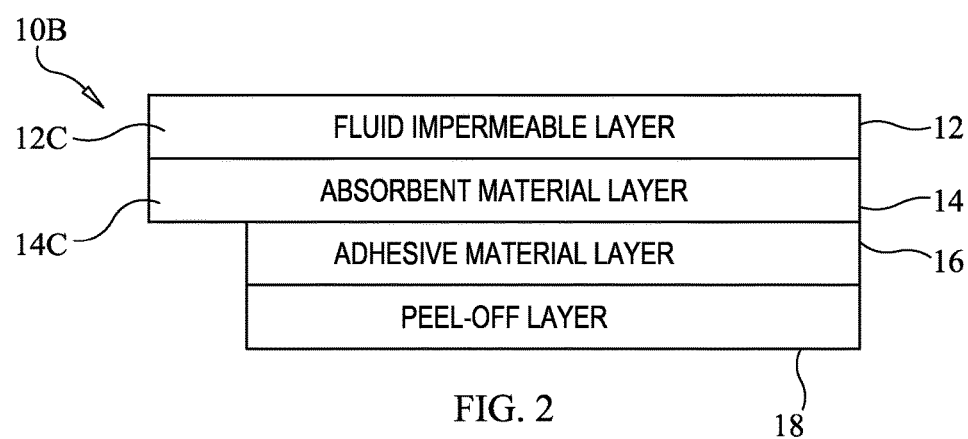
FIG. 2 is a schematic cross-sectional view of a multi-layer perspiration absorption and capture system prior to its use in accordance with another embodiment of the present invention.
Figure 3:
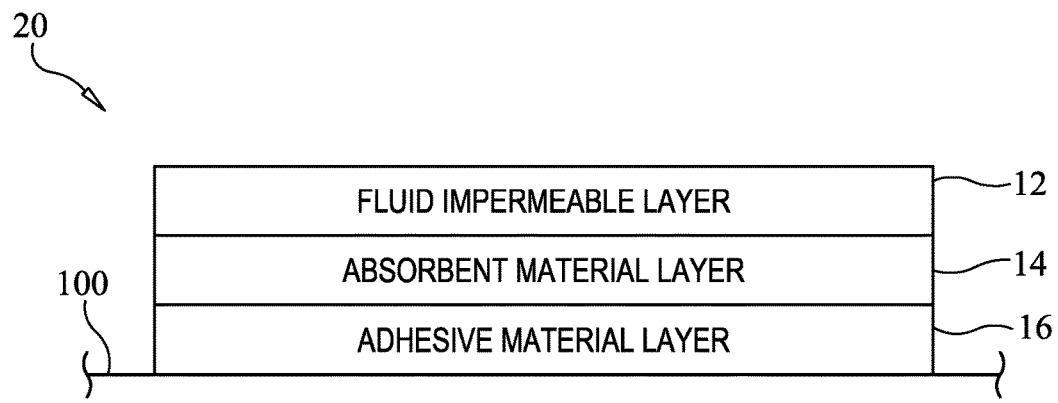
FIG. 3 is a schematic cross-sectional view of a multi-layer perspiration absorption and capture system adhered to a skin surface in accordance with an embodiment of the present invention.

Referring now to the drawings, simultaneous reference will be made to FIGS. 1-3 where a multi-layer perspiration absorption and capture system in accordance with the present invention is illustrated in schematic views. More specifically, FIGS. 1 and 2 illustrate embodiments of the perspiration absorption system in its pre-use state and are referenced generally by numeral 10A in FIGS. 1 and 10B in FIG. 2. FIG. 3 illustrates the perspiration absorption system in its use state where it's adhered to a skin region 100 and is referenced generally by numeral 20. As will be explained further below, the perspiration absorption system of the present invention can be configured for placement and coverage of a variety of skin regions without departing from the scope of the present invention.

In its pre-use state, perspiration absorption system 10A/10B includes four layers, while perspiration absorption system 20 in its use state includes three of the four layers from system 10A/10B. The three common layers are made from flexible-material layers, while the additional layer in pre-use system 10A/10B can be flexible or inflexible without departing from the scope of the present invention. The three common layers include a fluid impermeable layer 12 having an exposed face 12A and an opposing face 12B, an absorbent material layer 14 having one face 14A adjacent and coupled to face 12B of layer 12 and an opposing face 14B, and an adhesive material layer 16 having one face 16A adjacent and coupled to face 14B of layer 14 and an opposing face 16B exhibiting adhesive properties. Adhesive material layer 16 can be a distinguishable layer of material with just face 16B exhibiting adhesive properties, or it can exhibit adhesive properties throughout its thickness and be attached or integrated into layer 14 at least at face 14B without departing from the scope of the present invention. Layer 16 is a fluid permeable layer fabricated such that fluid can permeate through a solid sheet thereof, or through a sheet having one or more through holes. Layer 16 can also be realized by one or more selectively-placed regions of adhesive without departing from the scope of the present invention. Layers 12, 14 and 16 are coupled to one another by, for example, stitching, thermal bonding, adhesive bonding, etc. about the periphery or other regions thereof.

The fourth layer 18 of pre-use system 10A/10B is one that adheres to face 16B of layer 16 but can be peeled from face 16B without damage to layer 16. Accordingly, peel-off layer 18 is any of a variety of materials (e.g., wax paper, waxed paper, plasticized paper, and other release liner materials) known in the art that can achieve these functions.

Fluid impermeable layer 12 is a flexible material that prevents fluid/moisture from passing through surface 12A. In this way, absorbent material layer 14 is not exposed to environmental moisture so that the fluid absorbed by layer 14 only originates from the wearer's skin. In addition, the fluid absorbed by layer 14 is captured or locked into layer 14 since layer 12 is fluid impermeable. Suitable materials for layer 12 include, but are not limited to, polypropylene films, polyethylene films, polyvinylchloride films, etc.

Absorbent material layer 14 is a flexible material that absorbs fluid/moisture when exposed thereto. Layer 14 can be fibrous or non-fibrous without departing from the scope of the present invention. Suitable materials for layer 14 include, but are not limited to, super absorbent fiber materials, super absorbent polymer materials, magnesium carbonate, etc. Furthermore and as shown in FIG. 2 for pre-use system 10B, a small portion (or portions) of absorbent material layer 14 can extend beyond the periphery of layers 12, 16 and 18 to define one or more tabs 14C that facilitate removal of the system from a skin surface. Additionally or alternatively, a small portion (or portions) of fluid impermeable layer 12 can extend beyond the periphery of one or more of layers 14, 16 and 18 to define one or more tabs 12C that facilitate removal of the system form a skin surface.

Adhesive material layer 16 can be a flexible adhesive material throughout its thickness, but is adhesive at least at face 16B thereof. All of layer 16 (or at least face 16A) should comprise a hypoallergenic adhesive that can safely adhere to a human skin surface for the necessary period of time even when that skin surface is perspiring. Further, layer 16 must permit the passage of fluid/moisture through to absorbent material layer 14. Suitable materials for layer 16 include, but are not limited to, skin-friendly pressure-sensitive adhesive materials made from a variety of acrylic, silicone, synthetic rubber, and non-latex formulations.

Figure 4:
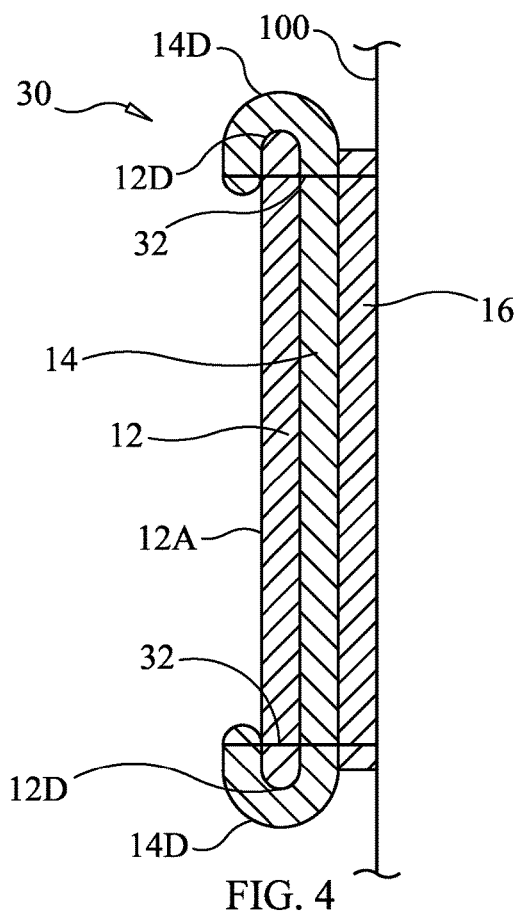
FIG. 4 is a cross-sectional view of a multi-layer perspiration absorption and capture system configured to absorb perspiration from the skin and from the face of the system in accordance with another embodiment of the present invention.

Referring now to FIG. 4, a cross-sectional view illustrating an embodiment of an in-use system adhered to skin region 100 is referenced generally by numeral 30. Accordingly, in-use system 30 includes just layers 12, 14 and 16 as described above. In the illustrated embodiment, absorbent material layer 14 extends beyond and is wrapped over the periphery 12D of fluid impermeable layer 12 as indicated at 14D where overwrap region 14D is in contact with face 12A. Layers 12, 14 and 16 are stitched together about the periphery of in-use system 30 as indicated by stitch lines 32. Assuming system 30 is frequently in an angular or vertical orientation such that perspiration (not shown) or atmospheric moisture (not shown) is flowing along skin region 100 towards system 30, overwrap region 14D of layer 14 absorbs such perspiration/moisture. In addition, overwrap region 14D absorbs any moisture that runs along face 12A of fluid impermeable layer 12. One or more of the above-described tabs 12C and/or 14C (not shown in FIG. 4) can also be provided at the periphery of fluid impermeable layer 12 and/or absorbent material layer 14, respectively.

Figure 5:
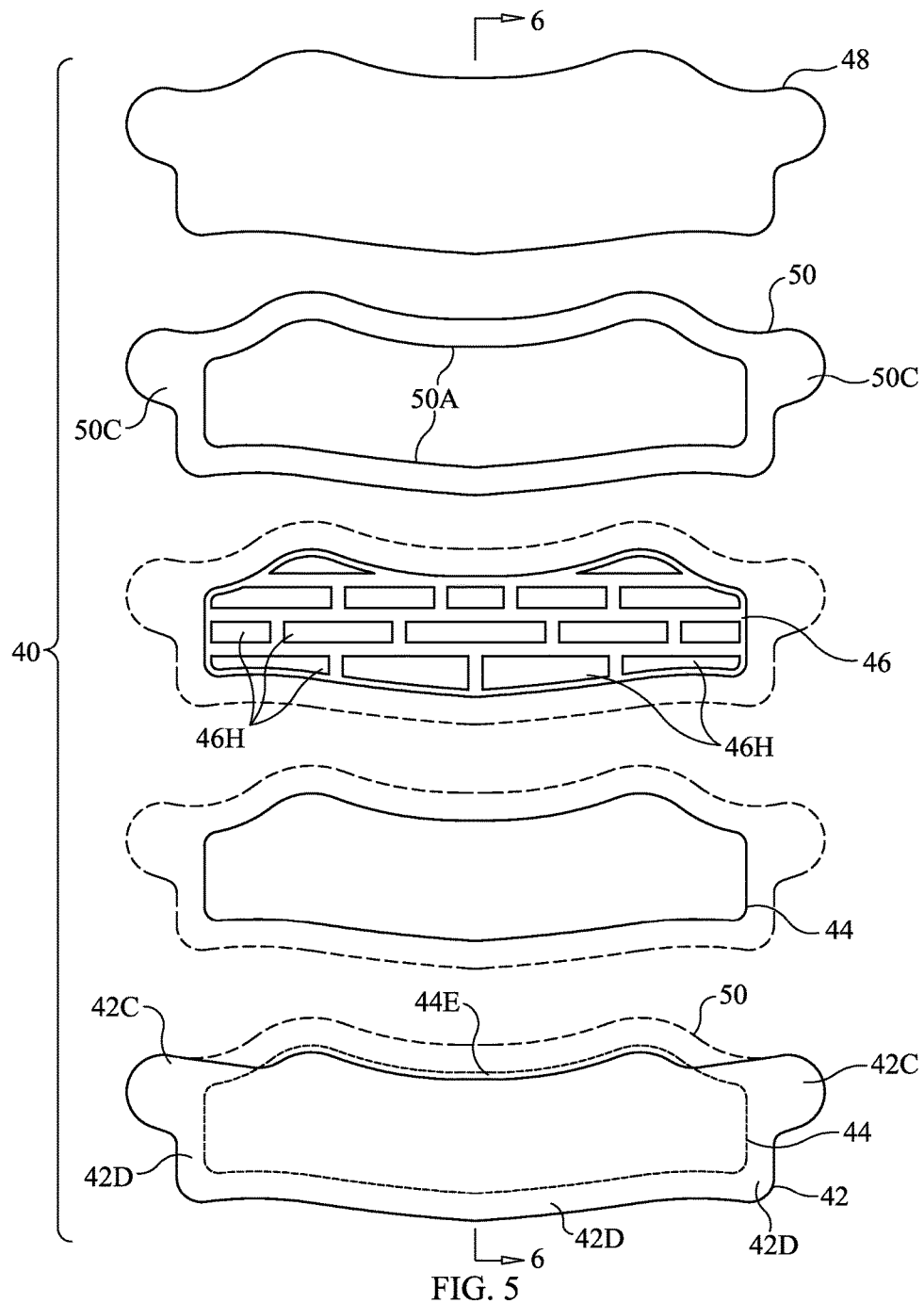
FIG. 5 is an exploded plan view of the layers in a perspiration absorption and capture system configured for placement on and coverage of a forehead in accordance with an embodiment of the present invention.
Figure 6:
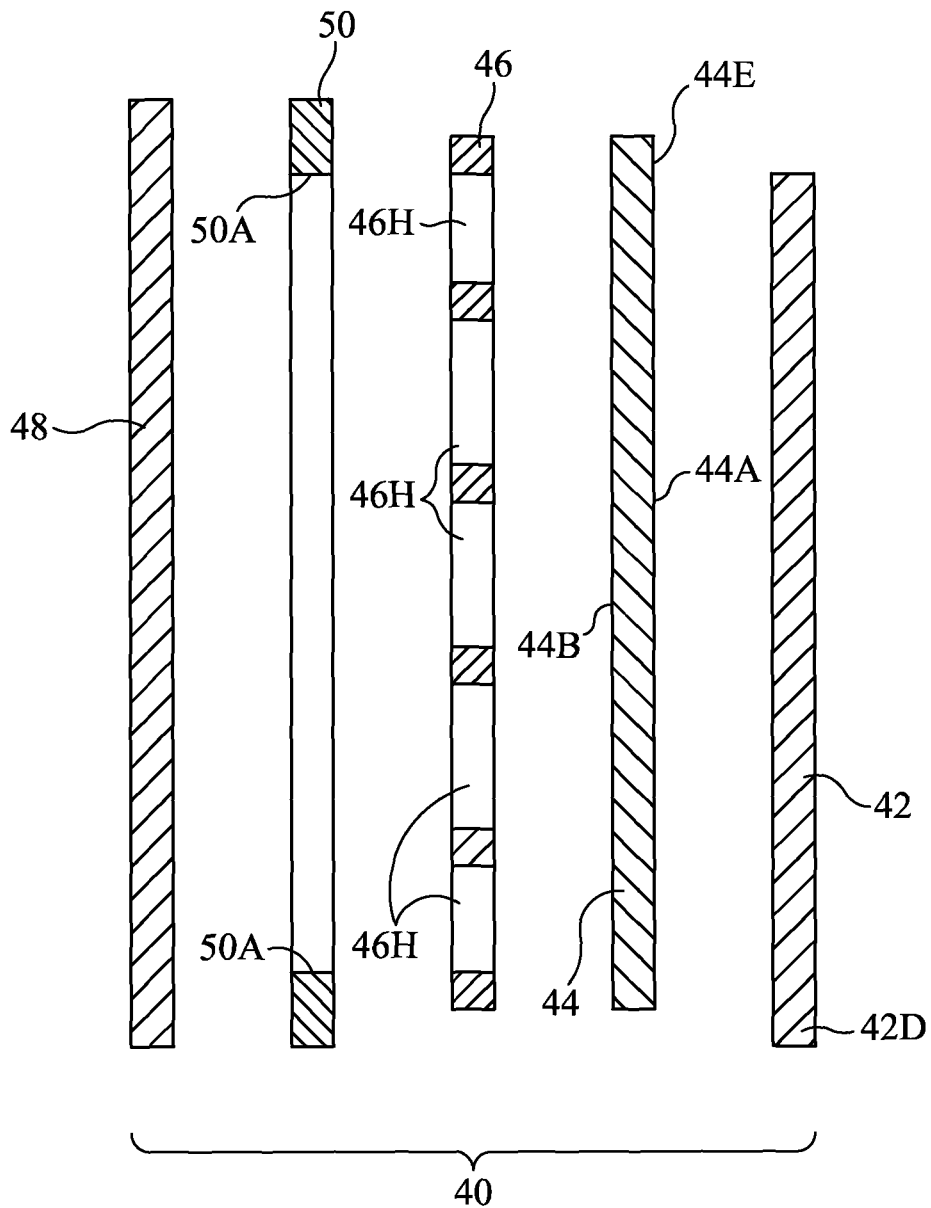
FIG. 6 is an exploded cross-sectional view of the layers taken along line 6-6 in FIG. 5.

Referring now simultaneously to FIGS. 5 and 6, another embodiment of the present invention is shown in an exploded plan view and an exploded cross-sectional view thereof, respectively. By way of an illustrative example, FIGS. 5 and 6 illustrate a perspiration absorption and capture system 40 sized/shaped for placement on and coverage of a user's forehead. FIG. 5 illustrates an exploded plan view of system 40 with each of the individual five layers being shown in isolation. The layers are arranged in a stack as will be described below. For each of the five layers, solid lines are used to indicate the outline of the structure comprising that particular layer, whereas dashed lines are used to indicate features of one or more of the other layers in order to show their relationships to the particular (solid-line) layer. In FIG. 6, an exploded cross-sectional view of system 40 (taken along line 6-6 in FIG. 5) illustrates the stacked arrangement of the layers shown in FIG. 5. It is to be understood that the thicknesses of the layers in FIG. 6 are exaggerated to simplify illustration of their features.

System 40 includes a fluid impermeable layer 42 that is analogous to previously-described fluid impermeable layer 12, a fluid absorption layer 44 that is analogous to previously-described absorbent material layer 14, a fluid permeable adhesive layer 46 that is analogous to previously-described adhesive material layer 16, a peel-off layer 48 that is analogous to previously-described peel-off layer 18, and a fluid impermeable frame 50. Peel-off layer 48 will be present only in the pre-use state of system 40. That is, peel-off layer 48 will be removed by the user when it is desired to place/adhere system 40 to one's forehead.

Fluid absorption layer 44 is coupled on one face 44A thereof to fluid impermeable layer 42. Fluid impermeable layer 42 almost completely covers fluid absorption layer 44. In the illustrated example, a portion or region 44E of the periphery of fluid absorption layer 44 remains uncovered or exposed for reasons that will be explained further below. The remainder of face 44 is completely covered by fluid impermeable layer 42. Fluid impermeable layer 42 extends beyond the unexposed periphery of fluid absorption layer 44 to define an extension region 42D. Extension region 42D can be enlarged in one or more places to define tabs 42C that are analogous to previously-described tabs 12C.

Coupled to the opposing face 44B of fluid absorption layer 44 is fluid permeable adhesive layer 46. For example, layer 46 can have a hypoallergenic adhesive applied to both sides of a thin flexible material. Layer 46 can be made permeable to fluid by providing one or more holes 46H there through. In the illustrated embodiment, layer 46 is defined by a lattice-like adhesive material layer. However, it is to be understood that the adhesive and fluid-permeable functions provided by layer 46 can be achieved in a variety of ways (e.g., different shapes/configurations of the layer, providing areas of adhesive, etc.) without departing from the scope of the present invention.

Fluid impermeable frame 50 can be made from the same material used for fluid impermeable layer 42. Frame 50 has a cutout region 50A sized to be slightly smaller than the size of fluid absorption layer 44, while the outer portion of frame 50 is sized to be slightly larger than fluid absorption layer 44. In this way, a good portion of frame 50 can be adhered/bonded/fused to extension region 42D of fluid impermeable layer 42. Frame 50 can include tabs 50C sized/shaped to align with tabs 42C. The aligned tabs can be adhered/fused/bonded together.

Prior to use of system 40, peel-off layer 48 adheres to adhesive layer 46 via cutout region 50A. Once peel-off layer 48 is removed, the adhesive properties of layer 46 are accessible via cutout region 50A. In the illustrated embodiment, exposed region 44E is positioned at the upper portion of one's forehead, i.e., adjacent the wearer's hairline. In this way, fluid absorption layer 44 is able to absorb perspiration running down from the wearer's head as well as perspiration originating from a wearer's forehead. The fluid impermeable layer 42 locks or captures the perspiration in system 40 so that no perspiration escapes therefrom even as fluid absorption layer 44 becomes saturated.

Figure 7:
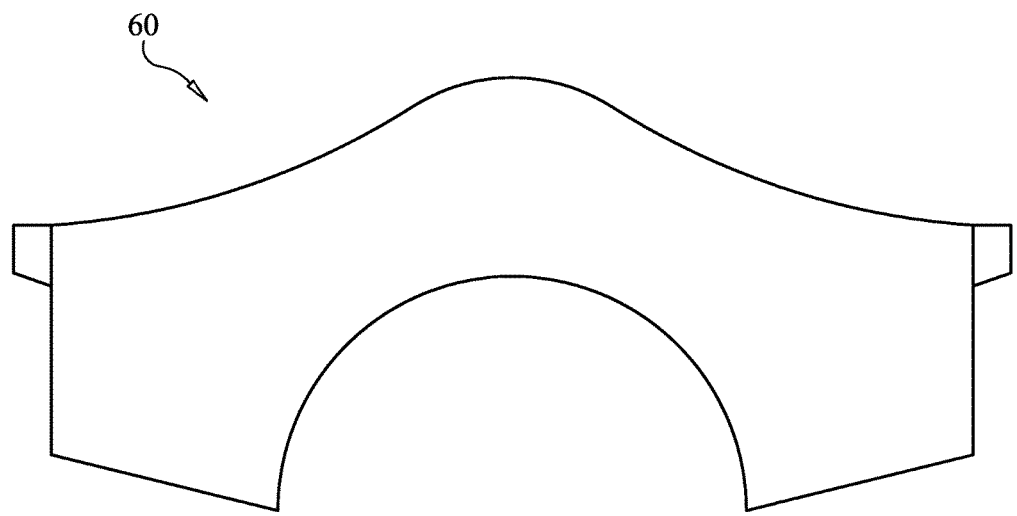
FIG. 7 is an outline of a perspiration absorption and capture system configured for placement on and coverage of a nose and upper cheek regions in accordance with another embodiment of the present invention.
Figure 8:
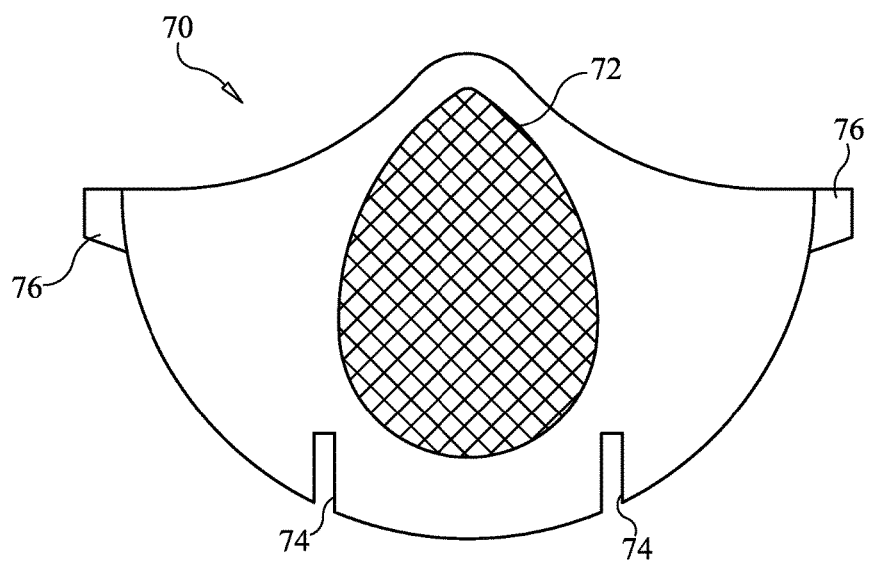
FIG. 8 is an outline of a perspiration absorption and capture system that incorporates a respiration filter/mask with the system being configured for placement on and coverage of a nose, cheek regions, mouth, and chin in accordance with another embodiment of the present invention.

As mentioned above, the skin-attached perspiration absorption system of the present invention can be configured (i.e., sized, shaped, etc.) for placement on and coverage of a variety of skin/body regions without departing from the scope of the present invention. By way of illustrative examples, several non-limiting additional configurations are illustrated in the system outlines of FIGS. 7-10 where each embodiment is constructed of multiple layers to include the features associated with one or more of the embodiments previously described herein. Referring first to FIG. 7, a perspiration absorption and capture system 60 is configured to cover the nose and upper cheek regions of one's face. FIG. 8 illustrates the outline of a perspiration absorption and capture system 70 that incorporates a respiration filter/mask 72 (e.g., simple paper or fabric filter, a filter with active filter elements, etc.) where system 70 can be placed on and cover one's nose, cheeks, mouth, and chin. One or more notches 74 can be provided in edges of system 70 to facilitate wrapping and adhesion to one's face (e.g., in the jaw and or chin regions of one's face). Tabs 76 can be provided to facilitate the removal of system 70 from one's face. In general, system 70 is constructed by framing filter/mask 72 with one of the flexible perspiration absorption and capture system structures described previously herein.

Figure 9:
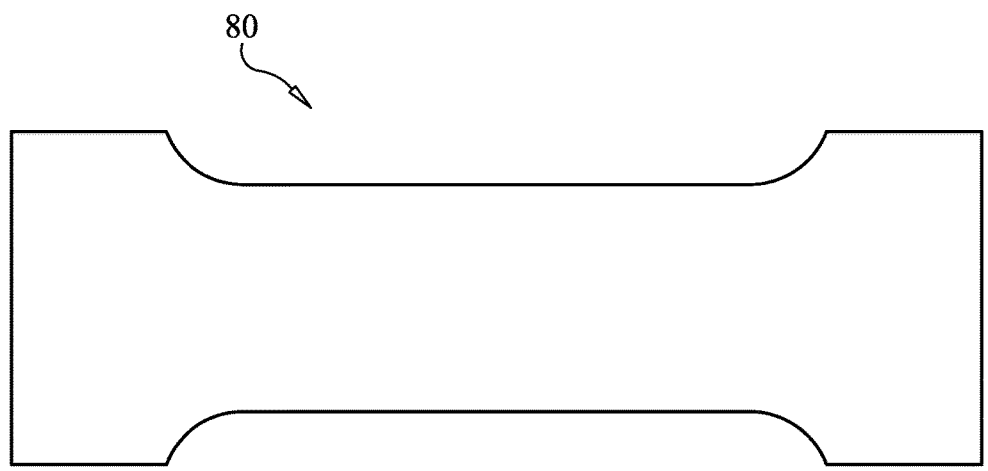
FIG. 9 is an outline of a perspiration absorption and capture system configured for placement of a non-facial region of the body in accordance with another embodiment of the present invention.
Figure 10:
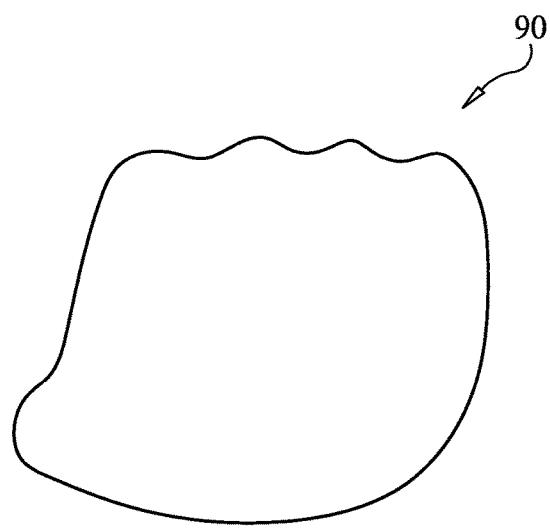
FIG. 10 is an outline of a perspiration absorption and capture system configured for placement on and coverage of a back-of-hand or palm region in accordance with another embodiment of the present invention.

The present invention is not limited to configurations that adhere to one's facial regions. For example, FIG. 9 illustrates the outline of a perspiration absorption and capture system 80 that is "I" shaped for adherence to one or more non-facial skin regions (e.g., the back of one's neck, underarm regions, etc.). The I-shape provides additional attachment and moisture absorption surface area while allowing the system to readily conform to a variety of body regions. FIG. 10 illustrates the outline of a perspiration absorption and capture system 90 configured for placement/coverage of the back of one's hand or palm region. System 90 allows a user to keep his fingers free for maximum dexterity. Accordingly, it is to be understood that the outline/shape of a perspiration absorption and capture system in accordance with the present invention can be realized by a variety of shapes/sizes without departing from the scope of the present invention.

The advantages of the present invention are numerous. The skin attached perspiration absorption and capture system can be readily adapted for use with a variety of skin surface regions. By absorbing perspiration/moisture from areas that are generally uncovered and/or located in places of great annoyance, the present invention can be used to improve comfort and/or safety for a variety of applications. The systems can be disposed of after use thereby ensuring that sanitary and contamination requirements are easily satisfied.

Although the invention has been described relative to specific embodiments thereof, there are numerous variations and modifications that will be readily apparent to those skilled in the art in light of the above teachings. For example, words, designs, and/or words and designs, can be printed on the exposed face of the fluid impermeable layer for functional reasons (e.g., to reflect light) and/or decorative reasons (e.g., advertising) without departing from the scope of the present invention. It is therefore to be understood that the invention may be practiced other than as specifically described.

What is claimed as new and desired to be secured by Letters Patent of the United States is:

1. A perspiration absorption and capture system, comprising:
    a fluid absorption layer having a first face and a second face, said fluid absorption layer having a peripheral edge;
    a fluid impermeable layer coupled to and covering said first face of said fluid absorption layer except for a portion of said first face of said fluid absorption layer adjacent said peripheral edge of said fluid absorption layer wherein said portion of said first face remains exposed, said fluid impermeable layer including an extension region thereof that extends beyond said peripheral edge over a remainder of said first face of said fluid absorption layer;
    a fluid permeable adhesive layer coupled to said second face of said fluid absorption layer; and
    a fluid impermeable frame coupled to said fluid permeable adhesive layer and coupled to said extension region of said fluid impermeable layer.

2. A perspiration absorption and capture system as in claim 1, wherein said fluid permeable adhesive layer comprises an adhesive material having a least one hole.

3. A perspiration absorption and capture system as in claim 1, further comprising a protective layer in removable engagement with said fluid permeable adhesive layer, wherein adhesive properties of said fluid permeable adhesive layer remain functional when said protective layer is removed from engagement with said fluid permeable adhesive layer.

4. A perspiration absorption and capture system as in claim 1, wherein said fluid impermeable layer and said fluid impermeable frame combine to define at least one tab extending beyond said peripheral edge of said fluid absorption layer.

5. A perspiration absorption and capture system as in claim 1, wherein an exposed surface of said fluid permeable adhesive layer comprises a hypoallergenic adhesive.

6. A perspiration absorption and capture system as in claim 1, wherein each of said fluid impermeable layer, said fluid absorption layer, said fluid permeable adhesive layer, and said fluid impermeable frame comprise flexible materials.

* * * * *